(12) United States Patent
Koh

(10) Patent No.: US 7,896,808 B1
(45) Date of Patent: Mar. 1, 2011

(54) SYSTEM AND METHOD TO SUPPRESS NOISE ARTIFACTS IN MIXED PHYSIOLOGIC SIGNALS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1421 days.

(21) Appl. No.: 11/301,452

(22) Filed: Dec. 13, 2005

(51) Int. Cl.
*A61B 5/00* (2006.01)
*A61B 5/04* (2006.01)
*A61B 5/08* (2006.01)
*A61N 1/00* (2006.01)

(52) U.S. Cl. .................. 600/300; 600/513; 600/529; 607/17; 607/20

(58) Field of Classification Search .......... 600/300, 600/513, 529; 607/18, 20
See application file for complete search history.

(56) References Cited

U.S. PATENT DOCUMENTS 4,677,986 A * 7/1987 DeCote, Jr. ............... 600/510

6,651,652 B1 11/2003 Ward .................... 128/200.24
7,200,436 B2 * 4/2007 Gilkerson et al. ............ 607/9

FOREIGN PATENT DOCUMENTS

EP 1 091 780 B1 6/2000
WO WO 00/00245 6/2000

* cited by examiner

*Primary Examiner*—Mark W Bockelman

(57) ABSTRACT

A system and method of sensing relatively low magnitude signals of interest in a sensing environment with at least intervals of relatively high magnitude noise of comparable or overlapping frequency spectra as the signals of interest. The systems and methods can be implemented in an efficient, low-power manner to facilitate long term monitoring of low magnitude physiologic signals, for example in an in vivo or implantable manner. An amplifier can be arranged with a threshold detector driving a normally closed switch such that the input to or output from the amplifier can be opened when the noise exceeds a threshold. A filter, such as a moving average filter, can be included to smooth the amplified output and compensate for the amplified signal lost when the threshold is exceeded. The systems and method facilitate implantable nerve sensing in high noise environments, such as from myopotentials.

10 Claims, 10 Drawing Sheets

SYSTEM AND METHOD TO SUPPRESS NOISE ARTIFACTS IN MIXED PHYSIOLOGIC SIGNALS

FIELD OF THE INVENTION

The invention relates to the field of medical devices and, more particularly, to in-vivo or implantable sensing of physiologically based signals, such as phrenic nerve sensing. The invention further relates to systems and methods of overcoming the confounding effects of relatively large magnitude noise signals present in the sensing environment to facilitate sensing of relatively low magnitude signals of interest.

BACKGROUND OF THE INVENTION

A variety of patient health ailments indicate continuous long-term monitoring of one or more types of physiologic activity. For example, many types of cardiac arrhythmia indicate ongoing monitoring of the patient's cardiac activity for indications that delivery of therapy is indicated. Sleep apnea is another health ailment where ongoing monitoring of the frequency and severity of occurrence of the condition is beneficial for improving the delivery of therapy and monitoring the progression of the condition. Cardiac arrhythmias can occur with symptoms that are not always readily observable or noticeable by the patient. As the name implies, sleep apnea occurs during sleep and patients suffering from this condition are also frequently unaware of the frequency and duration of occurrences of apneic episodes.

Thus, it is frequently preferable that a device or system be provided to the patient which automatically senses and monitors one or more physiologic processes related to the patient's health ailment to monitor conditions of which the patient may be unaware. As such conditions are frequently of a chronic nature indicating long term monitoring of the condition, it is preferable that such systems and devices for monitoring the condition be unobtrusive and convenient to employ for the patient. While external monitoring systems are quite useful and widely employed for short term use, such as for diagnosis or observation in a clinical setting, externally applied or worn appliances are generally disfavored by patients for the inconvenience to their bathing, dress, and other normal day-to-day activities. Thus, in many applications indicating long term monitoring of one or more physiologic processes, an implantable device which minimally interferes with the patient's bathing, clothing, etc. is often preferred. Such implantable devices are generally powered by long life batteries to extend the useful life of the device before battery replacement is required. Extended battery life is highly desirable as battery replacement requires an additional invasive surgical procedure.

A difficulty arises, however, with accurately sensing certain physiologic processes with a battery powered implantable device. In certain applications, a given physiologic activity may generate associated physical phenomena which can be referred to as signals corresponding to the underlying physiologic activity. Many types of physiologic activity generate signals which are of relatively low magnitude. For example, certain nerve activity may generate electrical signals on the order of one µV. Sensors, such as electrodes, can be applied to pick up these relatively low amplitude signals and convey these signals to appropriate amplifier and level detector circuits for further analysis. However, as the nerves are located within the patient's body cavity, other electrical signals arising from other physiologic activity is frequently communicated internally to the nerves or is otherwise or is otherwise detected by the sensors and constitutes noise.

Noise can be considered physical phenomena similar in nature to the signals which are of interest; however, the noise is of less or no interest in the sensing of the signals. Noise present in the sensing environment can confound the accurate sensing of the signals of interest. Noise is particularly troublesome when it has comparable or even greater magnitude and similar frequency characteristics or spectra as the signal of interest.

In one particular example, the phrenic nerves conduct electrochemical signals to the patient's diaphragm to drive the rhythmic contractions and relaxations of the diaphragm for the patient's cyclical respiration. The phrenic nerves generate electrical signals on the order of one µV. However, suitable preferred locations for placement of sensing electrodes on the phrenic nerves, such as adjacent the inferior vena cava (IVC) or the superior vena cava (SVC) are also adjacent the patient's heart. The cyclical depolarizations of the heart muscle create myopotentials that are on the order of one millivolt or more, e.g., of a thousand times or more greater magnitude than the phrenic nerve signal activity. The frequency spectra of the cardiac myopotentials are also comparable and overlapping to the nerve signals. Thus, accurately sensing from the phrenic nerves on an extended long term basis when it is not feasible to surgically expose and isolate the nerves is particularly challenging as the sensing environment is repeatedly exposed to noise that is many orders of magnitude greater than the actual signals of interest.

As the frequency spectra of the cardiac myopotentials is comparable and overlapping to that of the phrenic nerve signals, filtering techniques offer limited utility in suppressing the noise to accurately sense the nerve signals of interest. A variety of sophisticated signal recognition or detection algorithms are known, however, they are relatively demanding of computing capacity and generally require generally high rate sampling, on the order of 30 kHz or more. Implementing such relatively high rate sampling and executing sophisticated signal processing of algorithms is not generally feasible in an implantable device as the high sampling rate to implement such algorithms is too demanding of the limited battery power and would unacceptably shorten the useful life of the device.

Thus, it will be appreciated that there is an ongoing need for systems and devices capable of efficiently and accurately sensing relatively low magnitude signals of interest in a sensing environment which is exposed to relatively high magnitude noise of comparable and/or overlapping frequency spectra with the signals of interest. It would be a further advantage for such systems and devices to provide the desired improved performance in a relatively simple to implement and low cost manner. There is a particular need for systems and devices capable of supporting nerve sensing, including phrenic nerve sensing, on a long term in vivo or implantable basis, e.g. with a battery powered device.

SUMMARY

Various embodiments of the invention provide systems and methods to more accurately and efficiently sense relative low magnitude physiologic signals, such as nerve signals, in an environment which is at least at intervals exposed to relatively high magnitude background noise, such as from myopotentials. The systems and methods can be readily employed on a long-term and in vivo basis, such as with an implantable battery powered device. Certain embodiments include amplifying the low magnitude signals, suppressing the amplification of the noise when present, and analyzing the truncated amplified signals. In certain embodiments, the suppressing includes opening a normally closed switch on either the input or output of an amplifier to temporarily interrupt the amplification. A filter, such as a moving average filter, can be applied to the amplified output to smooth the rough morphology of the underlying signals as well as to compensate for the periods of amplification interruption.

Certain embodiments are primarily monitoring implementations. These implementations can include data storage and transmission capability such that long term monitoring of the patient can proceed and the data be stored and selectively be provided to an external device. Other embodiments include the monitoring as well as automatic therapy delivery. One particular embodiment provides phrenic nerve sensing to monitor respiratory demand. Upon observation that the phrenic nerve activity is indicative of CSA, overdrive pacing can be initiated or modified as therapy for the CSA. This embodiment would also typically include the capability to monitor and provide therapy for various cardiac arrhythmias as well.

DETAILED DESCRIPTION

Reference will now be made to the drawings wherein like numerals refer to like parts throughout. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
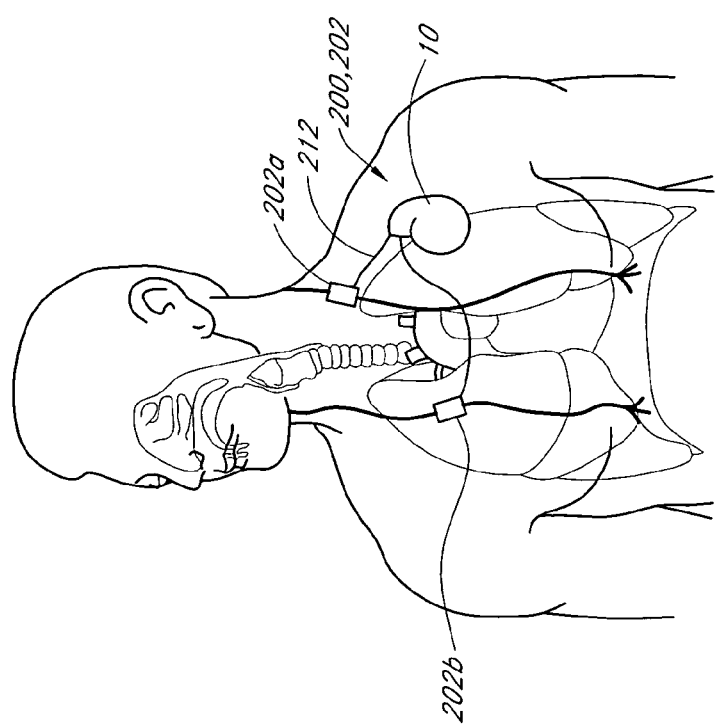
FIG. 1 illustrates one embodiment of an implantable physiologic signal sensing system.

FIG. 1 illustrates a patient provided with one embodiment of a medical device or system 200. The system 200 is adapted to accurately sense signals from physiologic activity which are of relatively low magnitude in an environment of relatively large magnitude noise. In the following description of the various embodiments of the invention, "signals" will generally refer to one or more monitored or sensed phenomena that are of interest and "noise" will generally refer to similar phenomena that are present in the same sensing environment, however are of less or no interest.

In certain embodiments, the system 200 is configured to sense signals from muscle activity of interest in an environment of background noise from other muscle activity that is not of direct interest. In one particular embodiment, the system 200 is configured to sense electrical signals arising from cardiac activity from implanted sensing sites which are also exposed to noise including myopotentials, such as from structural muscles and the diaphragm. In other embodiments, the system 200 is configured to sense nerve activity at one or more sensing sites that is also exposed to myopotentials, including myopotentials arising from cardiac activity constituting noise. Thus, depending on the particular application, a given physiologic phenomena can constitute noise or a signal.

Certain embodiments of the system 200 are adapted to sense the signals of interest in an efficient manner which reduces power consumption during the sensing process. Embodiments of the system 200 are also configured to more effectively isolate signals of interest from background noise, particularly when the noise is of relatively higher magnitude than the signals and of similar or overlapping frequency spectra.

The sensing system 200 comprises one or more physiologic sensors 202 which sense signals corresponding to underlying physiologic activity. In various embodiments, the one or more sensors 202 comprise temperature sensors, pressure sensors, voltage sensors, pH sensors, or other sensors selected for the physiologic activity of interest in the particular application. The embodiment of the system 200 illustrated in FIG. 1 is adapted to sense nerve signals of electro-chemical nature. In this embodiment, the sensors 202 are configured as electrical potential sensors or electrodes. In this embodiment, the system 200 comprises a first electrode assembly 202a which is implantable in a sub-clavian location to contact a first phrenic nerve. The system 200 also comprises a second electrode assembly 202b implantable adjacent the inferior vena cava (IVC) or the superior vena cava (SVC) to contact a second phrenic nerve. The electrodes 202a and 202b are arranged to pick up or sense time varying electrical potentials on the corresponding phrenic nerves.

The system 200 also comprises a signal processor 220 which receives signals from the electrode assembly(ies) 202 and analyses these signals. In one embodiment, the electrode(s) 202 conducts the signals to the signal processor 220 via one or more corresponding sensor leads 212. In this embodiment, the system 200 is configured as an implantable monitoring device to monitor activity on the phrenic nerves. In this particular embodiment, the system 200 is further adapted to function as a central sleep apnea (CSA) monitor. Thus, the signal processor 220 performs ongoing monitoring of activity sensed by the electrodes 202a and 202b for observation and analysis of the nature of the activity on the phrenic nerves for indications of episodes of CSA.

In this embodiment, the signal processor 220 also includes onboard storage or memory for recording data indicative of the observed activity on the phrenic nerves. The signal processor 220 also includes the capability to communicate this data, for example, via a telemetric link with an external device for further analysis by an attending clinician. Thus, in this embodiment, the system 200 provides sensing, analysis, storage, and communication capability, but lacks intrinsic therapeutic capability. Thus, in one embodiment, the system 200 automatically senses and records data indicative of the activity of a physiologic process, e.g., phrenic nerve activity, and can periodically communicate this data to an attending clinician to provide information related to the progress or severity of the patient's CSA. The clinician may then adjust therapy being provided to the patient, however, the therapy need not be directly provided by the system 200 itself.

Figure 2:
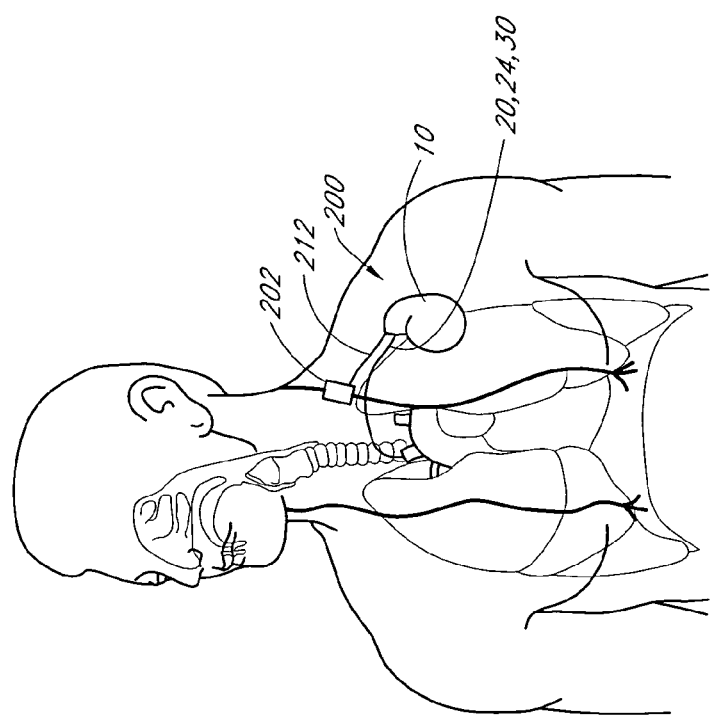
FIG. 2 illustrates another embodiment of an implantable physiologic signal sensing and therapy delivery system.

FIG. 2 illustrates another embodiment of a medical device 200 which includes the sensing, analysis, storage, and communication capability of the embodiment of the system 200 previously described with respect to FIG. 1. However, in this embodiment, the system 200 includes additional sensing capability as well as the ability to automatically provide therapy when indicated. More particularly, in this embodiment, the system 200 is further configured to sense and monitor the patient's cardiac activity and to provide appropriate therapeutic stimulations to one or more chambers of the patient's heart upon detection of a cardiac arrhythmia indicating therapy delivery. In this embodiment, the system includes a first sensor 202 which is configured as a nerve sensing electrode and which is arranged in a sub-clavian location to sense signals on the patient's left phrenic nerve. Of course, in other embodiments, additional sensors 202 may be included and arranged to sense activity on the right phrenic nerve and the exact location or positioning of the one or more sensors 202 can be adapted to the specific needs of the individual patient.

In this embodiment, the system 200 also includes an implantable medical device 10 which is interconnected with the first sensor 202 via a conducting sensor lead 212. The system 200 also comprises a plurality of cardiac leads 20, 24, and 30 which are also interconnected with the implantable device 10. The cardiac leads 20, 24, and 30 are provided at the opposite end with sensing/stimulation electrodes which will be described in greater detail below. The sensing/stimulation electrodes are configured to sense electrochemically based cardiac depolarization signals from the patient's heart and communicate these signals to the implantable device 10 for sensing of the patient's cardiac activity and detection of possible cardiac arrhythmias. Upon detection of a cardiac arrhythmia indicating therapeutic stimulation, the implantable device 10 initiates an appropriate electrical stimulation which is delivered by the corresponding cardiac leads 20, 24, and/or 30 for delivery to the patient's heart via the appropriate sensing/stimulation electrodes. Further details of the components and operation of the device 10 will be described in greater detail below.

As previously mentioned, in this embodiment, the system 200 includes the previously described capabilities to sense, analyze, store, and communicate to an external device data relating to the physiologic activity of the patient's phrenic nerve, as described for the embodiment of the system 200 illustrated with respect to FIG. 1. However, in this embodiment, the system 200 includes the capability to automatically provide therapy based not only on the observed cardiac activity, but also at least partly based on the observed activity of the phrenic nerve. For example, in one particular embodiment, the implantable medical device 10 can monitor the activity of the phrenic nerve via the first sensor 202 and the interconnecting sensor lead 212 for indications of CSA. Should the device 10 detect occurrences of CSA which may benefit from therapeutic intervention, the device 10 can institute delivery of such therapy on an automatic basis. In one particular embodiment, when the device 10 detects episodes of CSA, the device 10 can initiate delivery of atrial overdrive pacing as therapy for the CSA which has been shown to reduce CSA effects.

Figure 3:
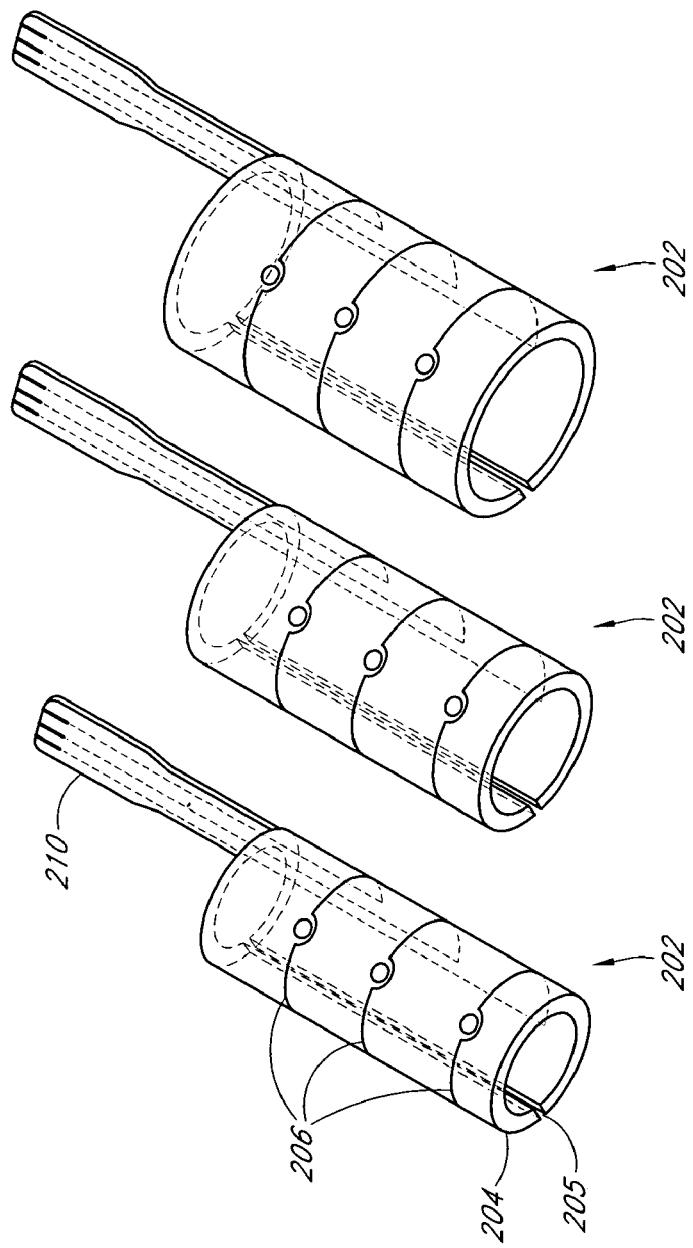
FIG. 3 illustrates several embodiments of implantable physiologic sensors.

FIG. 3 illustrates one embodiment of a sensor 202 in greater detail. In this embodiment, the sensor 202 comprises an electrode type sensor configured for in-vivo nerve sensing. In the embodiment illustrated in FIG. 3, three different sizes of nerve electrode assemblies 202 are shown which are sized and configured for sensing from nerves of various sizes. In this embodiment, the nerve electrode assemblies 202 comprise a flexible sleeve 204 which retains and supports one or more electrodes 206. In this embodiment, the nerve electrode assembly 202 comprises three separate electrodes 206 which are arranged to extend substantially circumferentially about a nerve positioned within the nerve electrode assembly 202. The electrodes 206 are also spaced apart from each other in a substantially equidistant manner and can thus provide the functionality, as desired depending upon the particular application, of sensing the direction of propagation of signals along the nerve. The electrodes 206 can also provide the capability of stimulating the nerve via the multiple separate electrodes 206, in certain embodiments. The nerve electrode assembly 202 also comprises a connector 210 in electrical communication with the electrodes 206 and wherein the connector 210 is configured for connection to one of the leads 212 (FIGS. 1 and 2).

In this embodiment, the sensor 202 comprises biocompatible materials which are also selected or suitably coated to reduce the susceptibility to corrosion during the implantation period. In this embodiment, the flexible sleeve 204 is also configured as a generally hollow cylindrical or tubular structure with a substantially axially extending slit or opening 205 extending substantially the length of the sensor 202. The flexible sleeve 204 and electrodes 206 are also comprised of a flexible material such that the nerve electrode assembly 202 can be splayed open along the slit or opening 205, wrapped around a nerve which is positioned within the sensor 202, and secured thereto, such as via suturing, stapling, and/or biocompatible adhesives.

In certain embodiments, the flexible sleeve 204 comprises a flexible and resilient material such that the sensor 202 can be splayed open and wrapped around a nerve such that, upon release, the nerve electrode assembly 202 resiliently bears on the nerve for attachment. It will be appreciated that the materials, sizes, configurations and attachment of the sensor 202 as well as the connection to and arrangement of the lead 212 is preferably selected to avoid application of undue pressure or stress to the nerve to avoid injury or degradation of function. Other embodiments of sensors suitable for use as nerve sensors in a relatively noisy sensing environment are described in greater detail in the co-owned application Ser. No. 11/045,626 filed Jan. 26, 2005 now U.S. Pat. No. 7,536,227 and entitled "Shielded Electrode for Nerve Sensing" which is incorporated herein in its entirety by reference.

Figure 4:
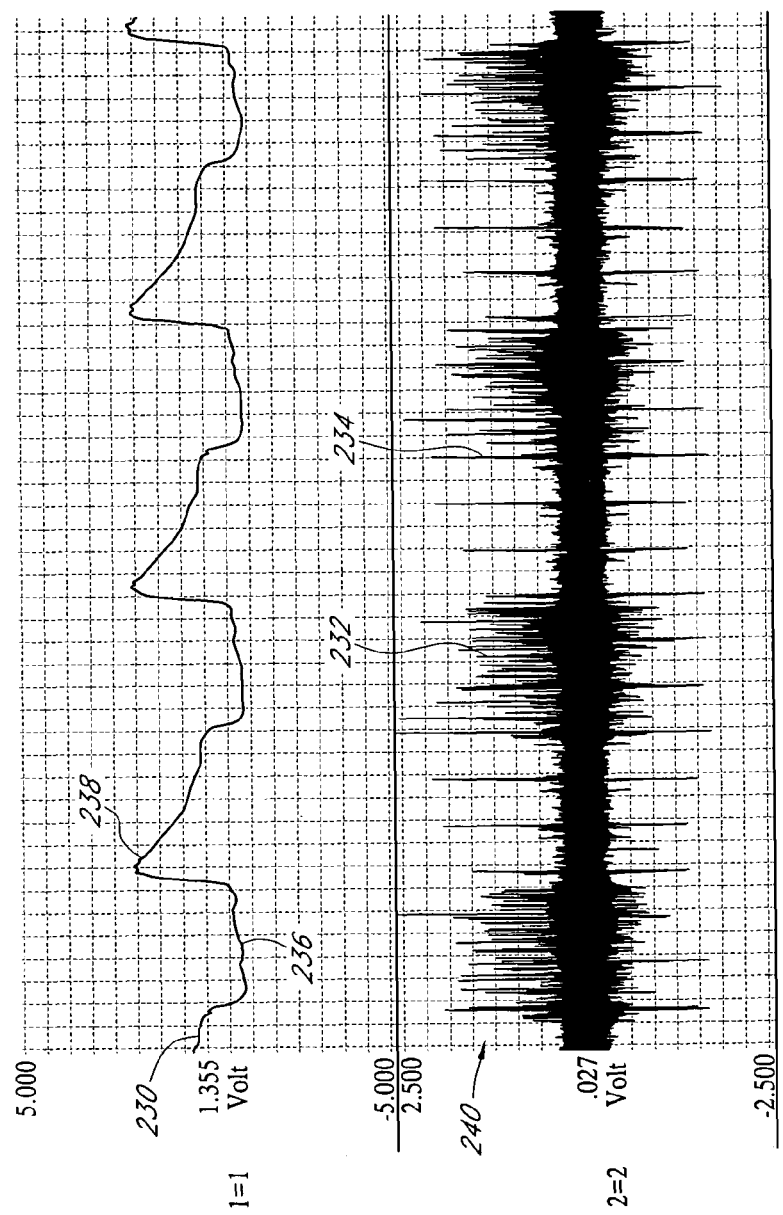
FIG. 4 illustrates waveforms corresponding to physiologically based respiration flow and cardiac activity.

As the sensor(s) 202 in use is generally arranged in an implanted location, the sensor 202 will be exposed to both the physiologic signals of interest as well as noise, such as noise from myopotentials. For example, FIG. 4 illustrates one embodiment of waveforms from first and second sensors 202 illustrating the time varying signals from corresponding first and second physiologic activities. A first physiologic activity signal 230 corresponds, in this embodiment, to the air flow of the patient's respiration. The first physiologic activity signal 230 exhibits cyclical alternating episodes of inspiration phases 236 and exhalation phases 238. FIG. 4 also illustrates a second physiologic activity signal 232 corresponding, in this embodiment, to the sensed phrenic nerve activity. It can be seen that the second physiologic activity signal 232 exhibits significant activity during the inspiration phases 236 with significantly reduced activity during the exhalation phases 238 when the phrenic nerve is not providing signals to the diaphragm to induce the diaphragm to contract, e.g., during the relaxation phases of respiration.

However, as the second physiologic activity signal 232 is sensed in an environment which is also exposed to noise, such as from myopotentials, the sensed second physiologic activity signal 232 is overlaid with a third physiologic activity signal 234 corresponding to the cardiac depolarizations of the patient's heartbeat. Thus, the second and third physiologic activity signals 232, 234 as sensed are combined or intermixed so as to define a mixed signal 240 including components both from the phrenic nerve activity and the depolarization signals of the patient's heartbeat. As would be expected from the nature of the underlying physiologic activity, the second physiologic activity signal 232 corresponding to phrenic nerve activity exhibits activity at a different rate or period than the third physiologic activity signal 234 corresponding to the patient's cardiac activity. In addition, the third physiologic activity signal 234, when active, is of significantly higher magnitude or amplitude than the second physiologic activity signal 232 corresponding to the phrenic nerve activity. Also, as previously noted, the second and third physiologic activity signals 232, 234 share significant similarities in their frequency spectra such that bandpass filtering offers very limited utility in separating or isolating the second physiologic activity signal from the third physiologic activity signal 232, 234.

Figure 5:
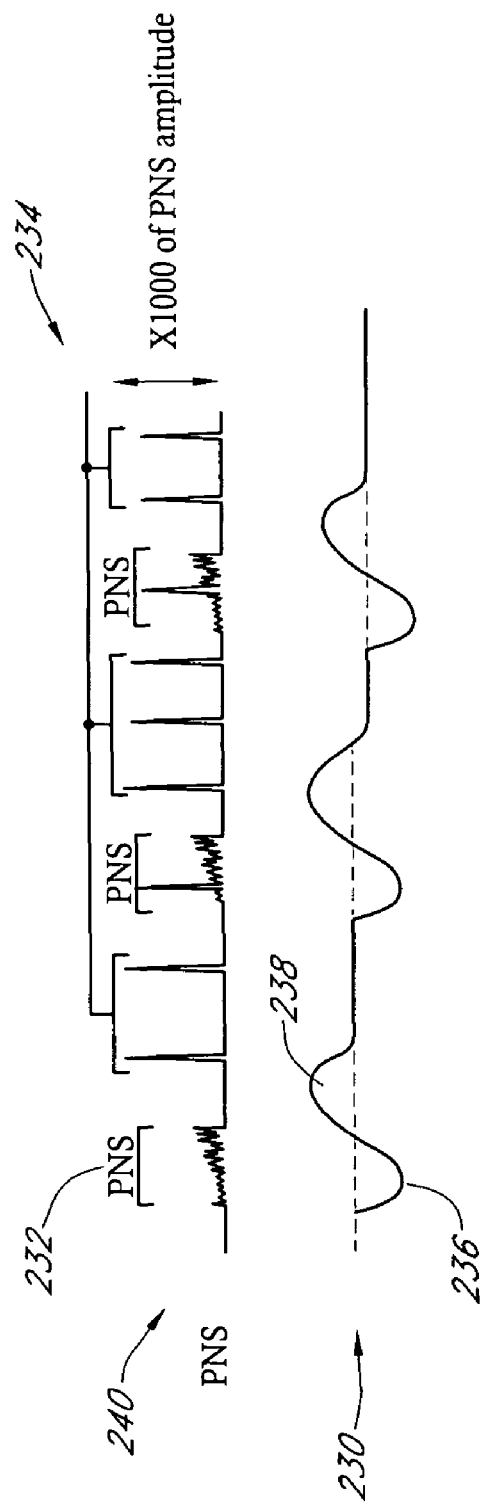
FIG. 5 illustrates one embodiment of a mixed physiologically based signal including components from phrenic nerve activity and cardiac activity with corresponding respiration throughout several inspiration and exhalation cycles.

FIG. 5 illustrates another example of wave forms corresponding to the first, second, and third physiologic activity signals, 230, 232, and 234. While not to scale, FIG. 5 illustrates schematically that the magnitude of the third physiologic activity signal 234 constituting a portion of the mixed signal 240 has an amplitude one thousand times or more greater than the amplitude of the second physiologic activity signal 232 portion of the mixed signal 240. FIG. 5 also illustrates that as the first and second physiologic activity signals 230, 232 correspond to respiration which operates independently at a different rate or period than the patient's cardiac activity indicated by the third physiologic activity signal 234, that at times the second and third physiologic activity signals 232, 234 will be active at different times and at other points in the cycles will occur in concert. Particularly during instances when the second and third physiologic activity signals 232, 234 occur at the same time, it can prove extremely difficult to discriminate the possible absence of activity of the second physiologic activity signal 232, for example, during an apneic episode. The relatively much stronger third physiologic activity signal 234 can mask or override the absence of the second physiologic activity signal 232 leading to a false negative error or a failure to note the absence of the second physiologic activity signal 232.

Figure 6:
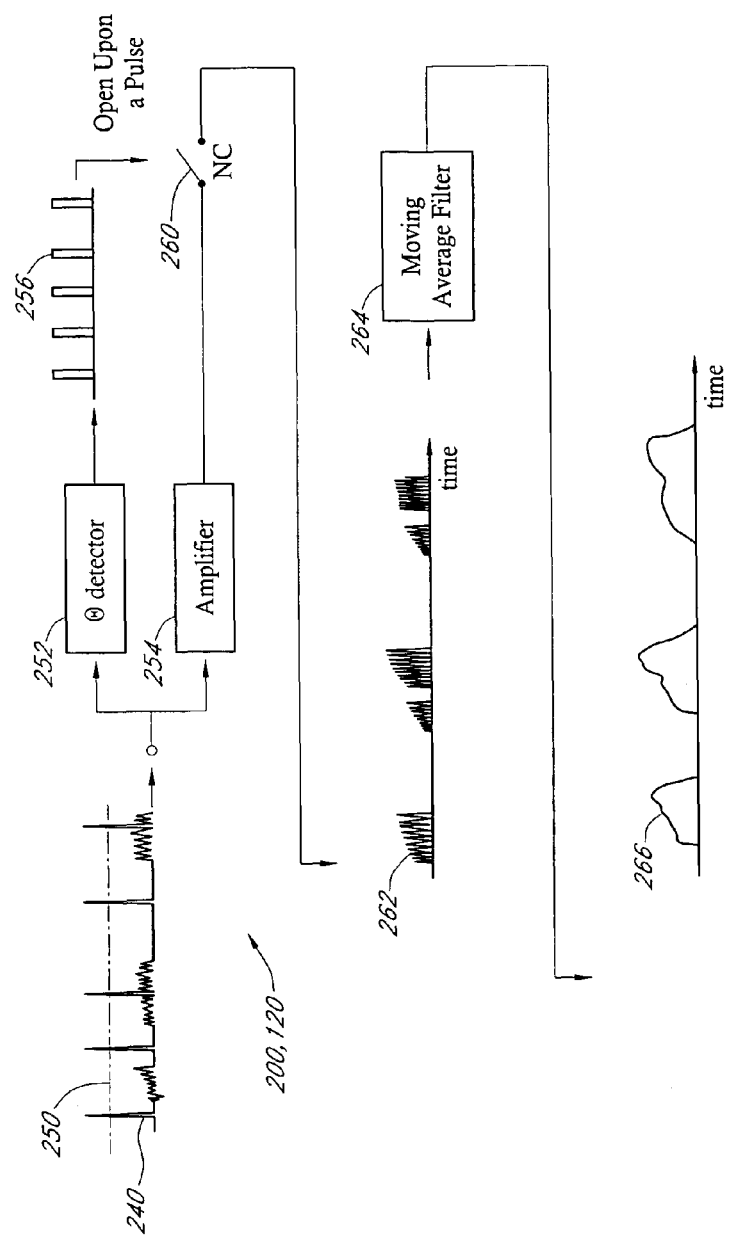
FIG. 6 illustrates one embodiment of a system to isolate a relatively low amplitude physiologic signal from background noise which is cyclically of relatively high magnitude.

FIG. 6 illustrates one embodiment of the system 200 to address the difficulty in accurately sensing a relatively low amplitude signal of interest in a mixed signal 240 including noise of relatively large amplitude. In this embodiment, the system 200 includes a signal processing module 120 that defines a threshold 250 which the mixed signal 240 would be expected to exceed at least intermittently, such as during periods of activity of the third physiologic activity signal 234. In this embodiment, the mixed signal 240 is provided to both a threshold detector 252 and an amplifier 254 arranged in parallel with threshold detector 252. The threshold detector 252 is programmed with the threshold value 250 such that during periods when the mixed signal 240 exceeds the threshold value 250, the threshold detector 252 provides output pulses 256 indicating that the mixed signal 240 has exceeded the threshold 250. The amplifier 254 amplifies the mixed signal 240 and provides this amplified output to a normally closed gate or switch 260. However, upon the output pulses 256 being active, the normally closed switch 260 is opened such that the output of the amplifier 254 is temporarily interrupted. Once the mixed signal 240 drops below the threshold value 250, the active output pulse 256 from the threshold detector 252 ceases and the normally closed switch 260 returns to its closed position.

Thus, the system 200 with the signal processing module 120 provides a noise suppressed signal or proxy signal 262 which comprises the amplified output of the mixed signal 240, however, with the intervals of the mixed signal 240 which exceed the threshold 250 gated out or removed from the noise suppressed signal 262 by the opening of the normally closed gate/switch 260. In one particular embodiment, the duration of the relatively high magnitude third physiologic activity signal 234 being active is relatively brief in comparison to the duration of the relatively lower magnitude second physiologic activity signal 232 being active. The noise suppressed signal 262, while having a portion of the second physiologic activity signal 232 in the mixed signal 240 lost by the opening of the normally closed switch 260, maintains a significant portion of the amplified underlying second physiological activity signal 232. The system 200 further accommodates or compensates for this partial loss of signal by providing the noise suppressed signal 262 with replacement values for the portion of the mixed signal which is removed or gated out. This can be implemented by a filter 264 which, in one particular embodiment, comprises a moving average filter. The filter 264 smoothes the output of the filter 264 to at least partially replace the absent noise in the noise suppressed signal 262.

The system 200 thus develops an amplified clean signal 266 from which the second physiologic activity signal 234 has been substantially removed and which has been smoothed by the filter 264. The amplified clean signal 266 thus provides a relatively smooth signal corresponding to the relatively high frequency underlying first physiologic activity signal 232. The amplified clean signal 266 can thus be further evaluated, for example, for evaluation of the patient's respiratory demand indicated by activity on the phrenic nerve, such as to monitor for episodes of CSA.

Figure 7:
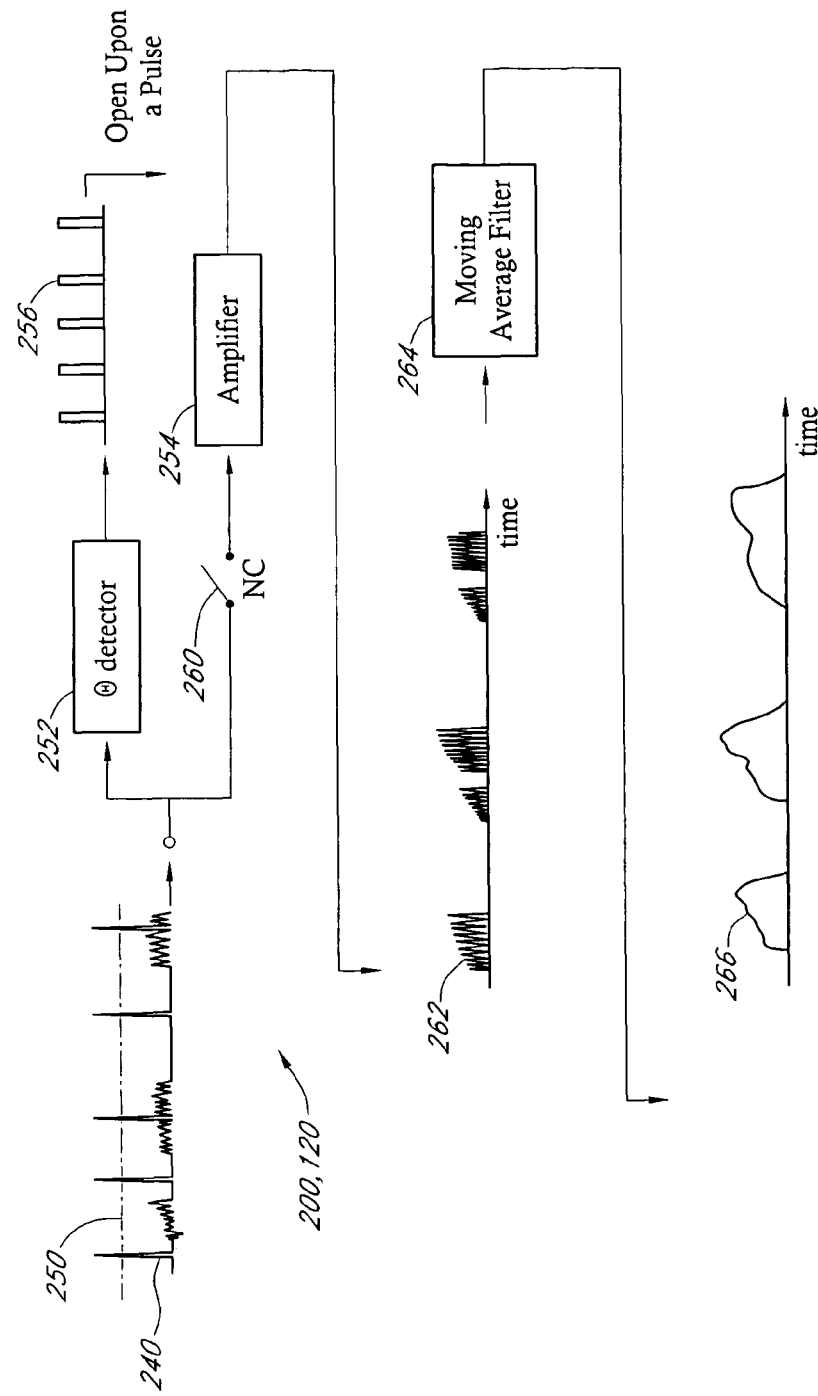
FIG. 7 illustrates another embodiment of a system to extract a relatively low amplitude physiologic signal of interest from a mixed signal which at least intermittently includes background noise which is of relatively high magnitude.

FIG. 7 illustrates another embodiment of a system 200 substantially similar in operation to the embodiment of the system previously described with reference to FIG. 6, however, with the placement of the gate or normally closed switch 260 differing. More particularly, in this embodiment, the normally closed switch 260 is arranged on the input side of the amplifier 254. The normally closed switch 260 is likewise in communication with the threshold detector 252 such that upon the mixed signal 240 exceeding the threshold 250, the threshold detector 252 provides an output pulse 256 to open the normally closed switch 260. Thus, during periods when the mixed signal 240 exceeds the threshold 250, the input to the amplifier is removed for a period of time such that the suppressed signal 262 again corresponds to an amplified signal comprising the second physiologic activity signal 232 with intervals when the third physiologic activity signal 234 is substantially absent.

Figure 8:
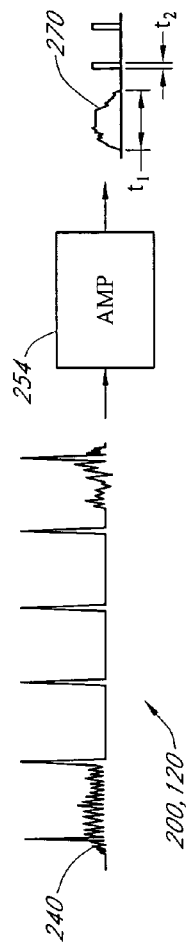
FIG. 8 illustrates yet another embodiment of a system to accommodate background noise which is cyclically of relatively high magnitude to facilitate processing of a relatively low amplitude physiologic signal.

FIG. 8 illustrates another embodiment of the system 200 with another embodiment of signal processing module 120 configured to more accurately sense the presence of a relatively low amplitude signal of interest from an environment of relatively high amplitude noise. In this embodiment, the mixed signal 240 is provided to an amplifier 254 in a similar manner to the embodiments of the system 200 previously described with respect to FIGS. 6 and 7. In this embodiment, however, the amplifier 254 is adjusted to amplify the mixed signal 240 such that the amplification provided by the amplifier 254 of the relatively low amplitude signals of interest in the mixed signal 240 are amplified so as to encompass a substantial portion of the dynamic range of the amplifier. In certain embodiments, the signals of interest are preferably amplified on the order of one thousand times for further processing in the system 200. The amplification characteristics of the amplifier 254 are selected such that, when the relatively high amplitude noise components of the mixed signal 240 are provided to the input of the amplifier 254, the output of the amplifier 254 saturates to generate a proxy signal accounting for the influence of the high magnitude noise.

This is indicated in FIG. 8 by the saturated amplified signal 270 where the amplified signals of interest in the mixed signal 240 substantially retain their morphology and relative values in the saturated amplified signal 270 when the high amplitude noise is substantially absent. However, during periods when the relatively high amplitude noise is present in the mixed signal 240, the saturated amplified signal 270 exhibits a constant saturated output from the amplifier 254.

In certain embodiments, the system 200 can further discriminate between the amplified signals of interest and the saturated amplified noise components of the mixed signal 240 by considering the duration or time period of the respective components. More particularly, the amplified signals of interest in the saturated amplified signal 270 will generally be active for a relatively elongated period indicated $t_1$. In contrast, the periods of saturation due to the noise components of the mixed signal 240 will typically be active for a relatively shorter period indicated as $t_2$. In the particular example of sensing respiration drive via the phrenic nerve in an environment exposed to cardiac-based myopotentials, the respiration signal driving inspiration will have a duration of approximately one to a few seconds. In contrast, the cardiac depolarization signals constituting a significant portion of the noise will have a duration on the order of a few hundred milliseconds or less. This embodiment of the system 200 as illustrated by FIG. 8 will generally indicate careful adjustment of the amplifier 254 to employ a significant portion of the dynamic range of the amplifier 254 in the amplification of the signals of interest and also the employing of an amplifier 254 which will readily tolerate repeated strong saturations when the noise components of the mixed signal 240 are present.

Figure 9:
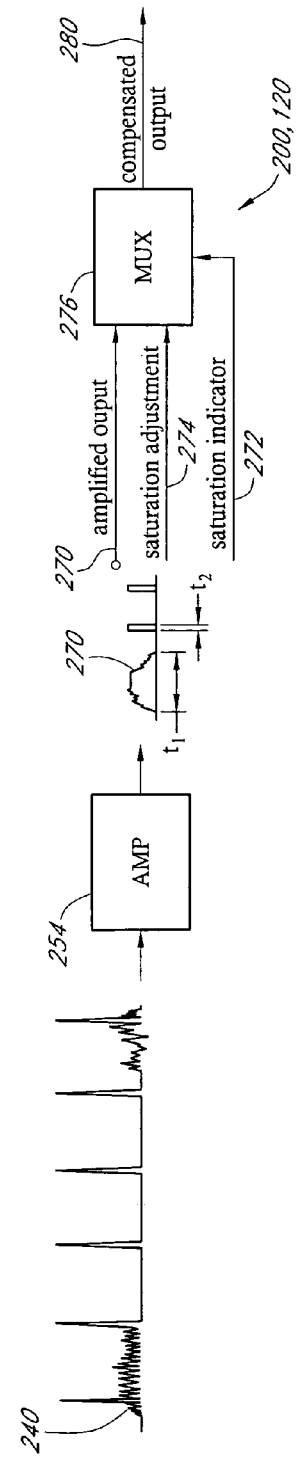
FIG. 9 illustrates a further embodiment of a system to compensate for the relatively high amplitude noise present in a sensing environment.

FIG. 9 illustrates yet another embodiment of a system 200 with yet another embodiment of signal processing module 120 adapted to accommodate or compensate for relatively high amplitude noise in a sensing environment. In this embodiment, the system 200 similarly receives a mixed signal 240 including both signals of interest as well as relatively high magnitude noise components. The mixed signal 240 is provided as an input to an amplifier 254 which is similarly adjusted to employ a significant portion of the dynamic range of the amplifier 254 in the amplification of the signals of interest. The output of the amplifier 254 will similarly comprise a saturated amplified output 270 which is intermittently saturated due to the relatively high magnitude of the noise components of the mixed signal 240. In addition, the amplifier 254 generates a saturation indicator 272 when the output of the amplifier 254 is saturated. This saturation indicator 272, as well as the amplified output 270 and a saturation adjustment 274, are provided as inputs to a multiplexer 276. The saturation adjustment signal 274 provides replacement signals to compensate for the periods of saturation of the amplified output 270.

In one particular embodiment, the saturation adjustment signal 274 comprises a fixed value which is selected to approximate the expected value of the amplified signal of interest when the output of the amplifier 254 is saturated due to the high amplitude noise. In another embodiment, the saturation adjustment signal 274 can comprise a multiple value compensation signal to provide variable adjustment or compensation depending on the presence or absence of the signal of interest in the mixed signal 240. For example, when the signal of interest is active, the saturation adjustment signal 274 is provided at a value to approximate the amplified signal of interest when the amplifier 254 saturates. During instances of noise and subsequent saturation of the amplifier 254 when the signal of interest is substantially absent, the saturation adjustment signal 274 can comprise a second significantly lower adjustment value to reflect the absence of the signal of interest in the mixed signal 240. Thus, in certain embodiments, the multiplexer 276 includes a comparison or comparator capability to evaluate the characteristics of the amplified output 270 prior to instances of saturation. The multiplexer 276 can thus provide a compensated output 280 which, at any time, comprises the amplified output 270 or the one or more saturation adjustment signals 274 depending on the presence or absence of the saturation indicator 272.

Figure 10:
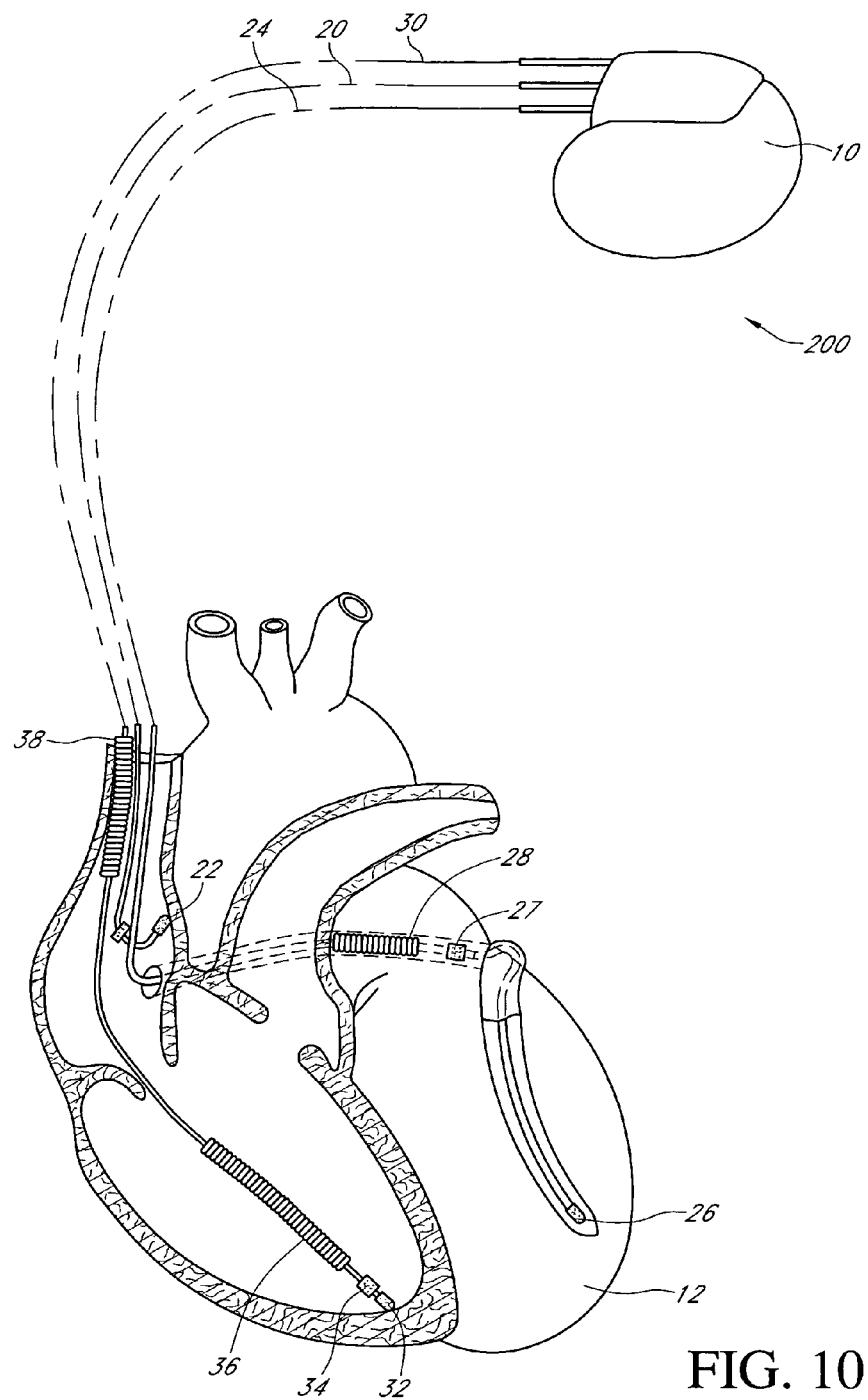
FIG. 10 is a simplified diagram illustrating an implantable stimulation device in electrical communication with at least three leads implanted into a patient's heart for delivering multi-chamber stimulation and shock therapy.

In one embodiment, as shown in FIGS. 2 and 10, the system 200 comprises an implantable cardiac stimulation device 10 in electrical communication with the patient's heart 12 by way of the three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 11:
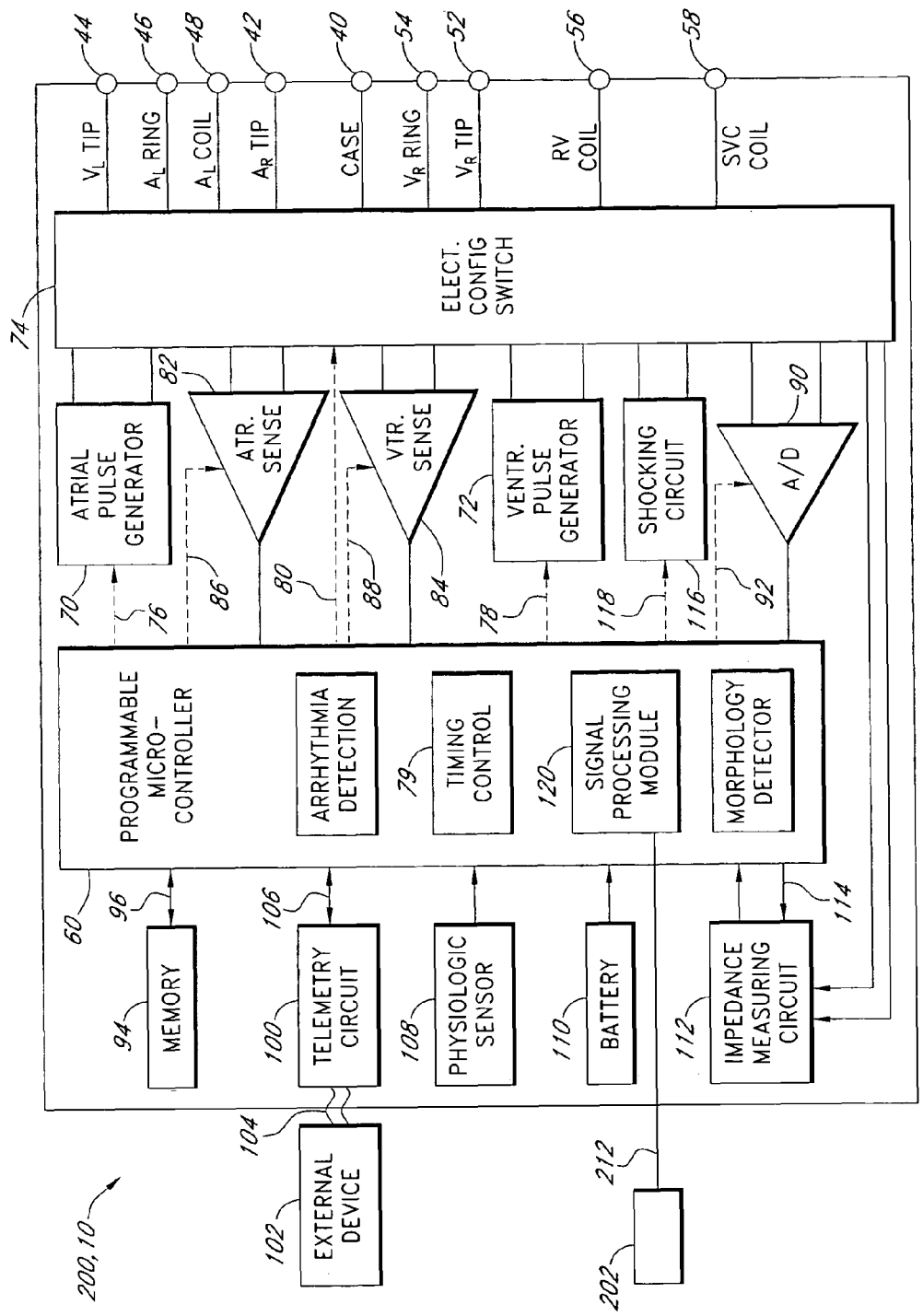
FIG. 11 is a functional block diagram of a multi-chamber implantable stimulation device illustrating the basic elements of a stimulation device which can provide cardioversion, defibrillation and pacing stimulation in four chambers of the heart.

As illustrated in FIG. 11, a simplified block diagram is shown of the multi-chamber implantable stimulation device 10 of the system 200, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 11, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 11, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals and convert the raw analog data into a digital signal. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96. The device 10 can thus store digital signals developed by the data acquisition system 90 for later processing and/or telemetric transmission to an external device 102. The programmable operating parameters used by the microcontroller 60 are also stored and modified in the memory 94, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

As previously described, in certain embodiments, the device 10 is also provided with signals from the one or more sensors 202. These signals are provided to one or more embodiments of the signal processing modules 120 previously described. The signal processing module 120 develops a processed signal, such as the amplified clean signal 266, the saturated amplified signal 270, or the compensated output 280. The microcontroller 60 can then evaluate the processed signals, such as phrenic nerve signals indicating respiratory drive for possible indications of CSA. Other embodiments of systems and methods for energy efficient signal sensing and processing which can be advantageously employed with the embodiments described herein can be found in the co-owned application Ser. No. 10/870,367 filed Jun. 16, 2004 and entitled "Implantable Medical Device With Nerve Signal Sensing" which is incorporated herein in its entirety by reference.

The stimulation device additionally includes a battery 110 which provides operating power to all of the circuits shown in FIG. 11. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. The embodiments of the system 200 described herein also extend the useful life of the battery 110 while facilitating additional sensing capabilities.

As further shown in FIG. 11, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Thus, in certain embodiments, the nerve sensing system 200 monitors nerve activity to improve delivery of therapy, such as pacing therapy, that is not necessarily directly related to the observed nerve activity. In other embodiments, the nerve sensing system 200 also monitors nerve activity and provides therapy, such as overdrive pacing to the heart 12, as therapy for conditions such as CSA to attempt to restore more desirable activity patterns for the observed nerve, such as the phrenic nerves. In yet other embodiments, the nerve sensing system 200 monitors nerve activity and provides, when indicated, therapy to the observed nerve and/or corresponding enervated tissue to supplement an observed deficiency in the nerve activity.

Thus the various embodiments of the system 200 described herein provide the capability to more efficiently suppress or isolate high magnitude noise present with a relatively low amplitude physiologic signal of interest on a long-term basis, e.g. with an implantable system 200. The system 200 can maintain a high degree of signal fidelity while accommodating the high amplitude noise in an energy efficient manner to extend the life of a battery 110 powering the system 200.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable medical device comprising:

one or more implantable sensors arranged to sense first physiologic signals having a varying first magnitude in the presence of second physiologic signals having a second magnitude that varies with respect to the first magnitude and is at least at certain intervals greater than the first magnitude of the signals;

a controller receiving sensed signals from the one or more sensors so as to receive a mixed signal including components from both the first and second physiologic signals; and a signal processing module arranged with respect to the one or more sensors such that the module provides an amplified signal to the controller and wherein, during intervals that the second physiologic signals exceed a threshold, the signal processing module suppresses amplification of the mixed signal provided to the controller so that the controller can evaluate the first physiologic signals with significantly reduced presence of the second physiologic signals;

wherein the signal processing module comprises an amplifier providing the amplified signal, a threshold detector, and a switch arranged such that, upon the mixed signal exceeding the threshold, the threshold detector induces the switch to open and interrupt the amplified signal to the controller and, upon the mixed signal dropping below the threshold, the threshold detector induces the switch to close such that the amplifier again provides the amplified signal to the controller.

2. The implantable device of claim 1, wherein the one or more sensors are configured to sense electrochemically based physiologic signals.

3. The implantable device of claim 2, wherein the one or more sensors are configured to sense nerve signals.

4. The implantable device of claim 3, wherein the nerve signals comprise phrenic nerve signals and wherein the controller evaluates the phrenic nerve signals for sensing of respiration.

5. The implantable device of claim 1, wherein the switch is arranged in a post-amplifier position.

6. The implantable device of claim 1, further comprising a filter to which the amplified output is provided to smooth the amplified output.

7. The implantable device of claim 6, wherein the filter comprises a moving average filter.

8. The implantable device of claim 1, further comprising data storage and a communications link in communication with the controller such that the device can store data indicative of the physiologic signals and communicate the data to an external device.

9. The implantable device of claim 1, further comprising a therapeutic stimulation generator in communication with the controller and configured to selectively deliver therapeutic stimulations based at least in part on the second physiologic signals such that the second physiologic signals constitute signals of interest with respect to the delivery of therapeutic stimulations and noise with respect to the sensing of the first physiologic signals.

10. The implantable device of claim 1, wherein the signal processing module comprises an amplifier providing the amplified signal wherein the amplifier has a dynamic range of amplification that is configured such that the first magnitude substantially encompasses the dynamic range such that when the second physiologic signals are active, the mixed signal saturates the amplifier.

* * * * *